United States Patent
Heitel et al.

(10) Patent No.: US 10,898,377 B2
(45) Date of Patent: Jan. 26, 2021

(54) HYBRID OPHTHALMIC INTERFACE APPARATUS

(71) Applicant: AMO Development, LLC, Santa Ana, CA (US)

(72) Inventors: Robert G. Heitel, Laguna Beach, CA (US); Charles C. Vice, San Juan Capistrano, CA (US); Hon M. Lee, Ladera Ranch, CA (US)

(73) Assignee: AMO Development, LLC, Santa Ana, CA (US)

( * ) Notice: Subject to any disclaimer, the term of this patent is extended or adjusted under 35 U.S.C. 154(b) by 411 days.

(21) Appl. No.: 15/789,720

(22) Filed: Oct. 20, 2017

(65) Prior Publication Data
US 2018/0036168 A1 Feb. 8, 2018

Related U.S. Application Data

(62) Division of application No. 14/198,353, filed on Mar. 5, 2014, now Pat. No. 9,795,509.

(60) Provisional application No. 61/799,981, filed on Mar. 15, 2013.

(51) Int. Cl.
*A61F 9/008* (2006.01)
*A61F 9/009* (2006.01)

(52) U.S. Cl.
CPC .............. *A61F 9/008* (2013.01); *A61F 9/009* (2013.01)

(58) Field of Classification Search
CPC ............................................. A61F 9/008–009
USPC ........................................................ 606/4–6
See application file for complete search history.

(56) References Cited

U.S. PATENT DOCUMENTS

| | | | |
|---|---|---|---|
| 6,019,472 A | 2/2000 | Koester et al. | |
| 6,254,595 B1 | 7/2001 | Juhasz et al. | |
| 2002/0103481 A1 | 8/2002 | Webb et al. | |
| 2007/0093795 A1 | 4/2007 | Melcher et al. | |
| 2009/0137989 A1 | 5/2009 | Kataoka | |
| 2009/0182310 A1 | 7/2009 | Gertner et al. | |
| 2009/0182312 A1 | 7/2009 | Gertner et al. | |
| 2010/0022994 A1 | 1/2010 | Frey et al. | |
| 2010/0274228 A1* | 10/2010 | Mrochen ................. A61F 9/009 | 604/541 |
| 2011/0022035 A1 | 1/2011 | Porter et al. | |
| 2011/0319873 A1 | 12/2011 | Raksi et al. | |

(Continued)

OTHER PUBLICATIONS

International Search Report and Written Opinion for Application No. PCT/US2014/020848, dated Nov. 11, 2014, 16 pages.

*Primary Examiner* — Nathan J Jenness
(74) *Attorney, Agent, or Firm* — Johnson & Johnson Surgical Vision, Inc.

(57) ABSTRACT

Apparatus and methods are provided for interfacing an ophthalmic surgical laser with an eye using a patient interface (PI). The PI may include a closed, fluid-filled bladder having fiducials that contacts and deforms to the eye. Or, the PI may have an applanation lens with an outer ring portion and an inner concave portion for receiving the apex of the cornea. Another PI features a suction ring with a flexible skirt for contacting the sclera that is non-circular and/or non-planar. A system for injecting an index matching fluid into the area above the eye may also be incorporated. An integrated system includes a co-molded lens cone and attachment ring, with a lens window at the bottom of the lens cone which provides a sealed volume for vacuum-attaching a laser delivery system above the lens cone.

13 Claims, 10 Drawing Sheets

(56) References Cited

U.S. PATENT DOCUMENTS

| | | |
|---|---|---|
| 2012/0016349 A1 | 1/2012 | Brownell |
| 2012/0283557 A1 | 11/2012 | Berlin |
| 2013/0041354 A1 | 2/2013 | Brownell et al. |
| 2013/0053837 A1 | 2/2013 | Kandulla et al. |
| 2013/0103014 A1 | 4/2013 | Gooding et al. |

* cited by examiner

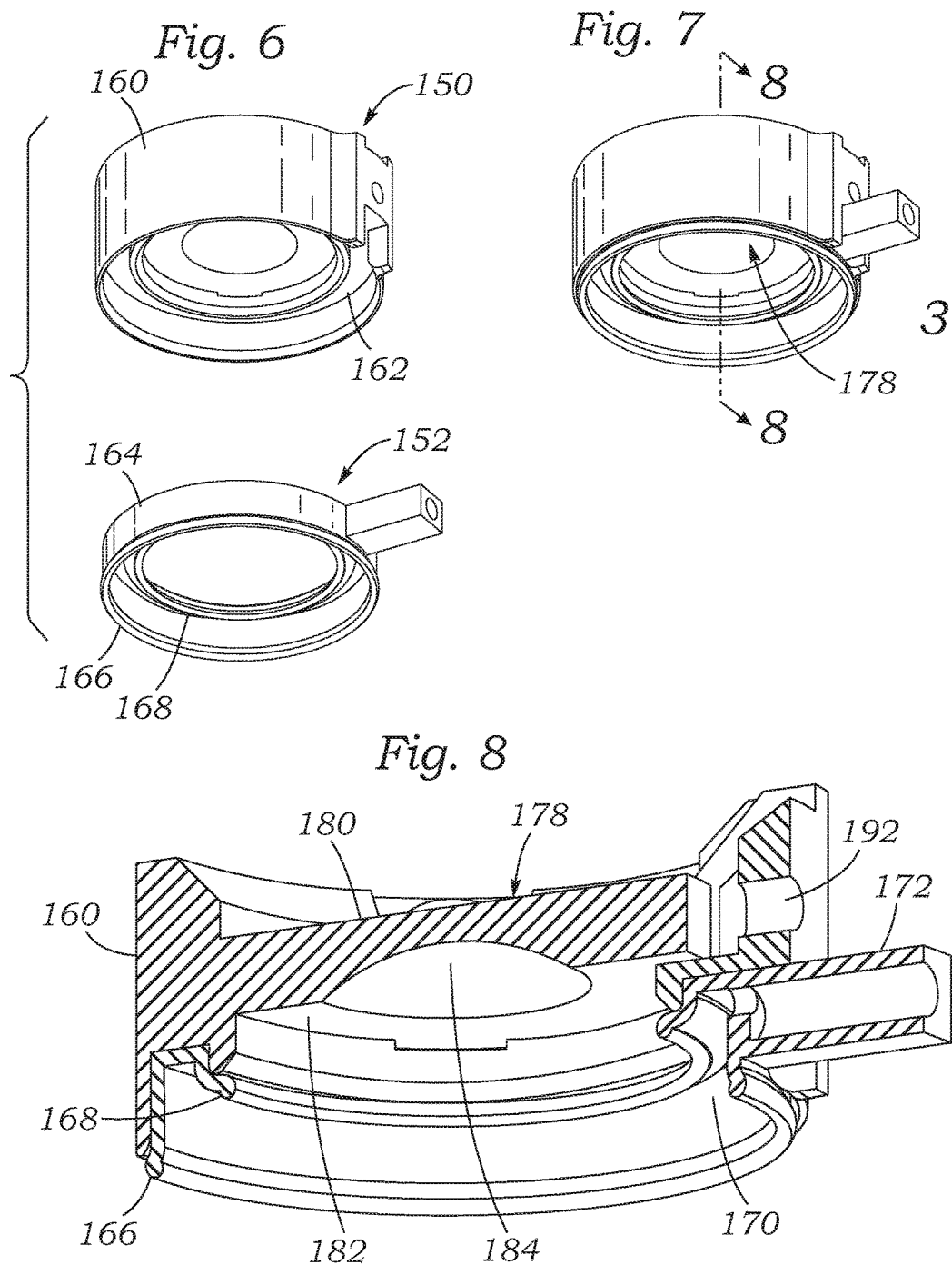

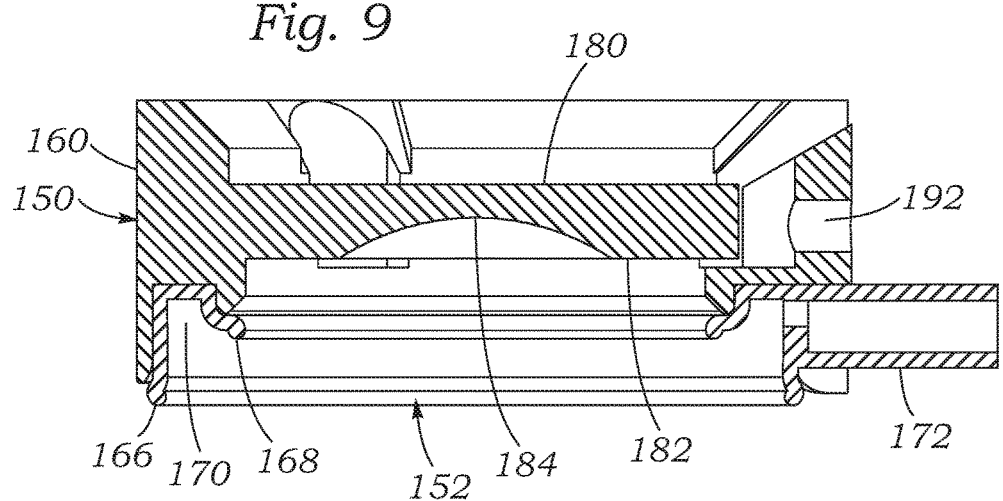
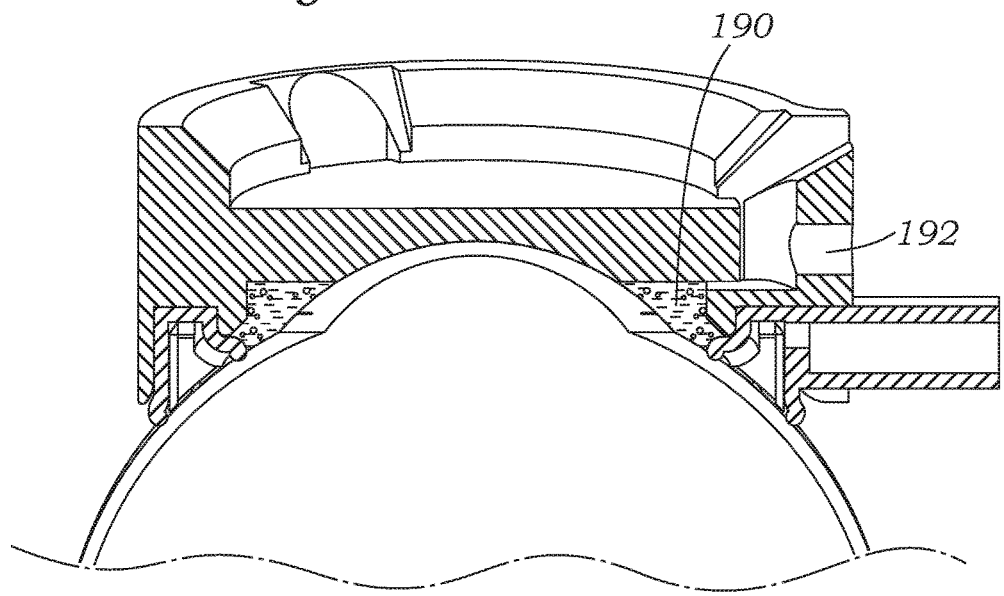

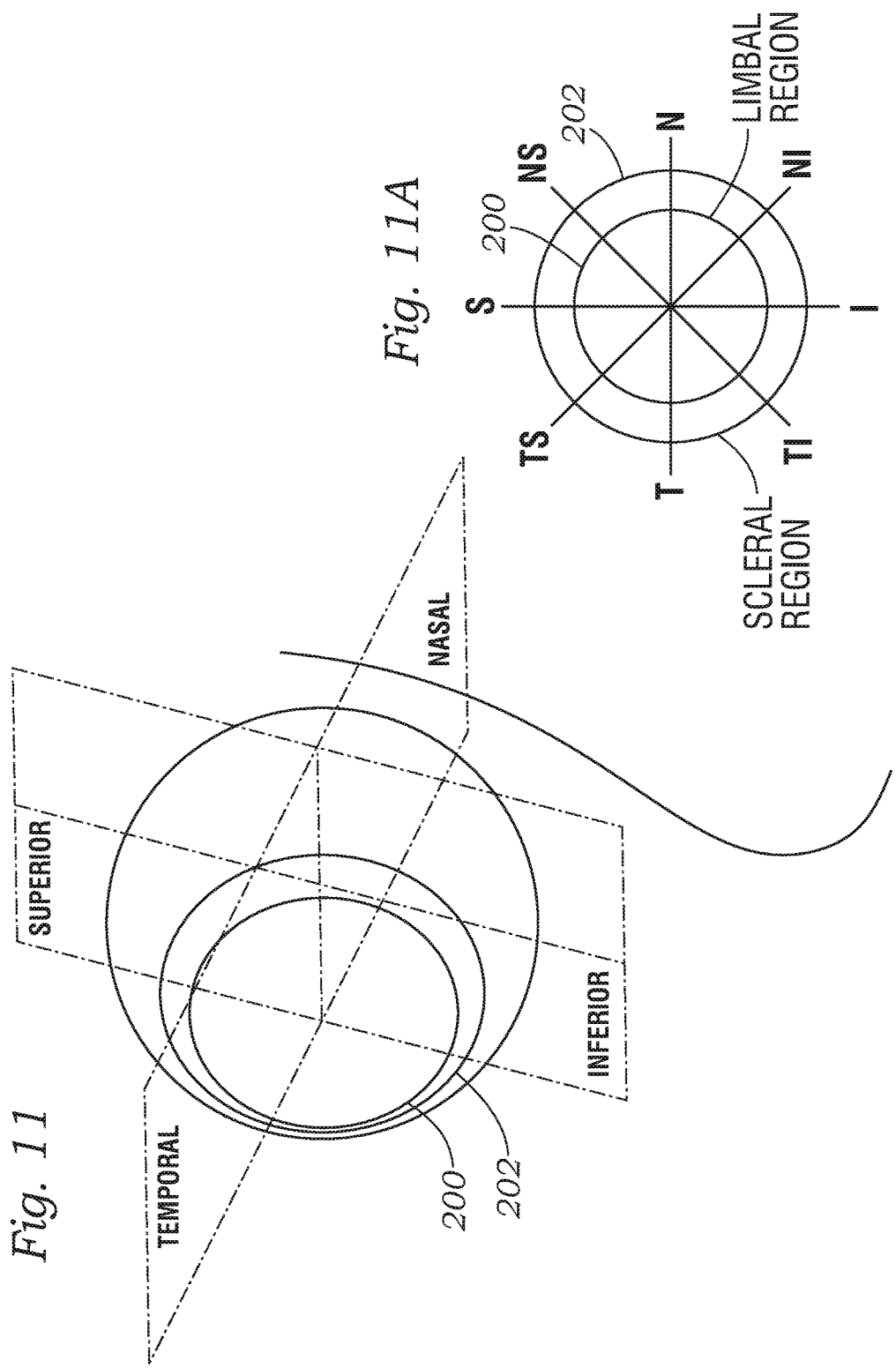

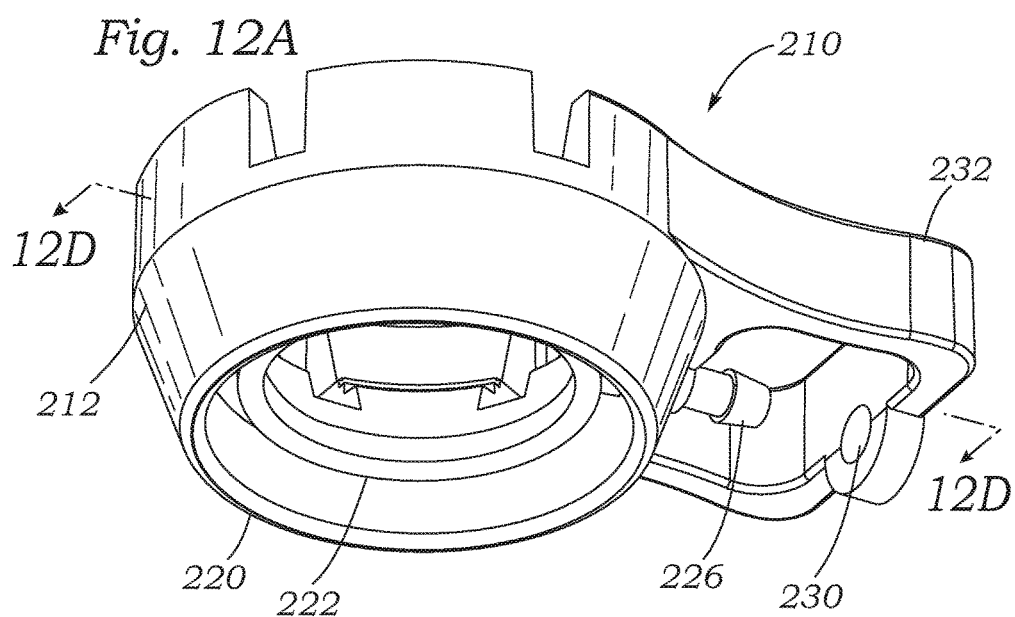
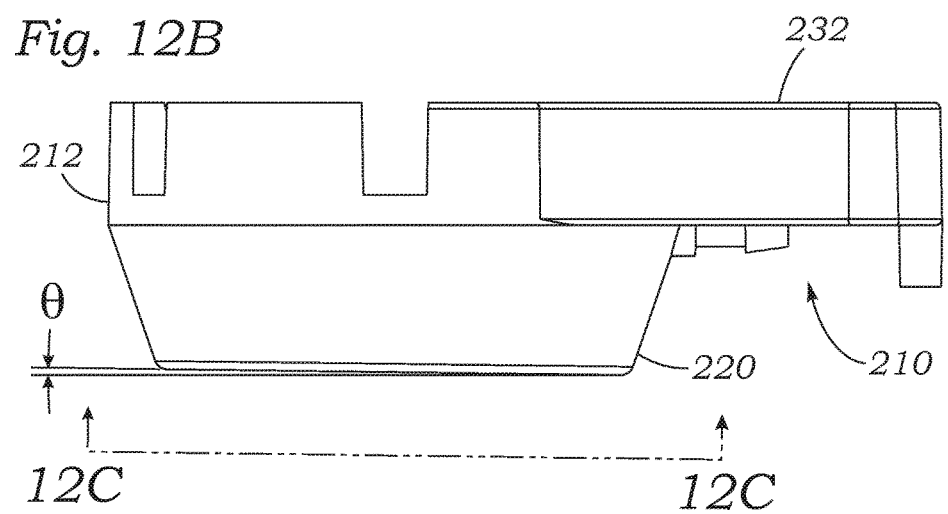

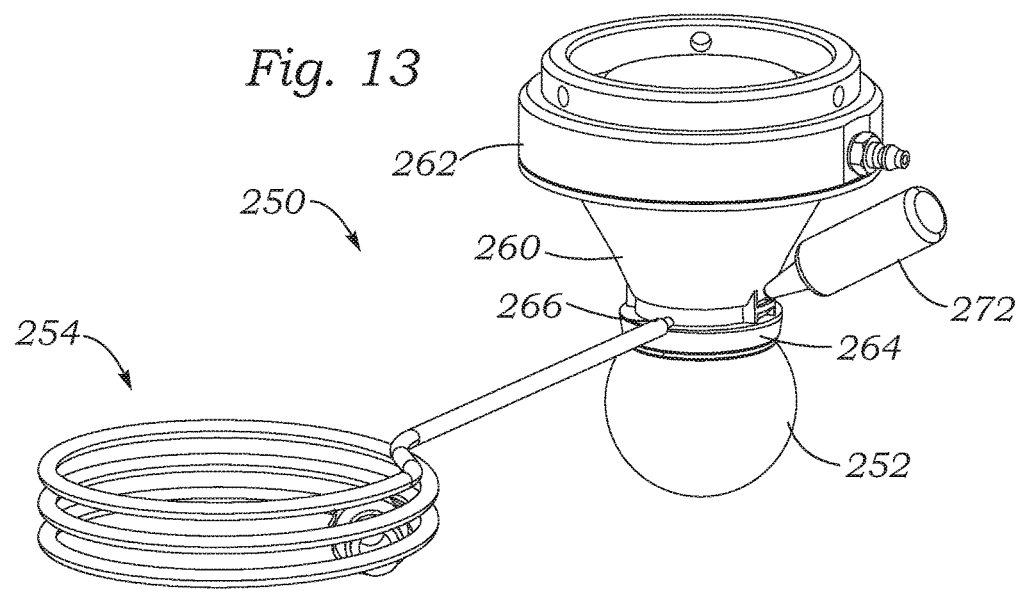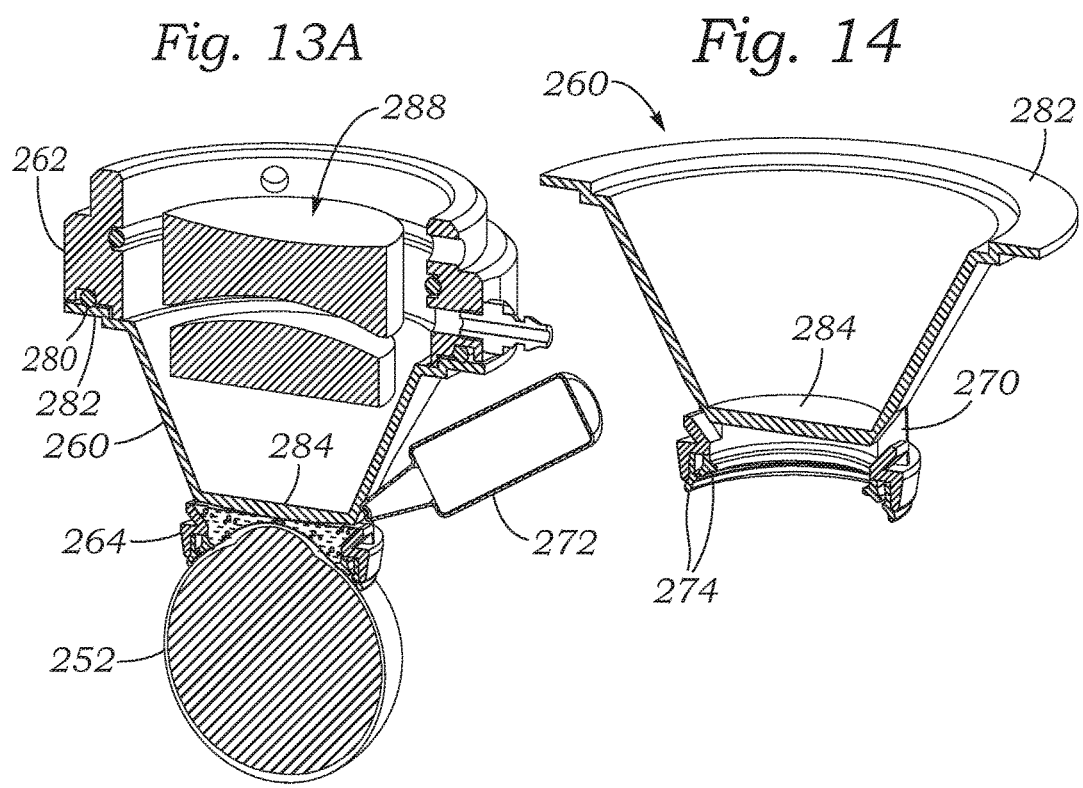

HYBRID OPHTHALMIC INTERFACE APPARATUS

CROSS-REFERENCES TO RELATED APPLICATIONS

This application is a divisional of and claims priority to U.S. application Ser. No. 14/198,353, filed on Mar. 5, 2014, which claims priority to U.S. provisional application No. 61/799,981 filed on Mar. 15, 2013, the entire contents of which are incorporated herein by reference.

TECHNICAL FIELD

Embodiments of this invention relate to ophthalmic laser surgery and, more particularly, to an ophthalmic interface apparatus used to stabilize the eye of a patient with respect to a laser beam during ophthalmic surgery, a and system and method of interfacing the eye with a surgical laser.

BACKGROUND

In recent years, significant developments in laser technology have led to its application in the field of ophthalmic surgery. In particular, laser surgery has become the technique of choice for ophthalmic surgical applications. In certain ophthalmic laser procedures, surgeons use a mechanical device termed a microkeratome to cut a layer of the anterior surface of the cornea in order to expose the underlying corneal stroma to which the laser is applied. However, complications surrounding the use of the microkeratome with a metal blade have resulted in research into improved techniques that are performed exclusively by a laser system. Such all-laser techniques provide significant improvements over conventional mechanical devices.

Despite these advances in laser technology, the use of such systems for ophthalmic surgical procedures remains fraught with substantial mechanical limitations, particularly in the area of developing a stable interface between an incident laser beam and the eye of a patient. Ophthalmic surgery is a precision operation and requires precise coupling between the surgical tool (i.e., the laser beam) and the region to be disturbed (i.e., a portion of the patient's eye). Movement of the eye with respect to the intended focal point of the laser beam can lead to non-optimal results and might result in permanent damage to non-renewable tissue within the eye. Given that eye movement is often the result of autonomic reflex, techniques have been developed in an attempt to stabilize the position of a patient's eye with respect to an incident laser beam.

One technique used to compensate for relative eye motion with respect to an incident laser beam is to have the patient focus on a stationary target. This involves providing a visual target to the eye undergoing surgery, and requiring that the patient retain focused on the perceived target feature. While this technique has provided some benefit, the patient bears a significant burden of minimizing relative motion. This technique is also less tolerant of any significant gross autonomic reflex motions, e.g., as when the patient might be startled. In this technique, the target provides an optical interface, while the patient's conscious responses provide the feedback mechanism.

Another technique involves the use of an optical eye tracking apparatus, whereby a selected eye feature is targeted for monitoring by an optical device. As the targeted feature displaces as a result of eye movement, this displacement is characterized and fed into the incident laser beam control apparatus as a compensation signal. This technique offers a substantial improvement over the first, particularly when implemented in addition to a patient-driven target focusing mechanism. However, such systems are inordinately expensive since a second, completely independent optical path is typically provided between a patient's eye and a surgical apparatus in order to accommodate the eye tracking apparatus. Further expense and complexity is incurred since an eye tracking apparatus requires an additional software component in order to be operative, which software component must be integrated into a laser delivery system. Considerations of interoperability must be met as well as the provision for an automatic shutdown of the laser system in the event of the loss of target feature lock.

Mechanical stabilization devices have been proposed, for example, a corneal applanation device, which is the subject of U.S. patent application Ser. No. 09/172,819, filed Oct. 15, 1998, and commonly owned by the assignee of embodiments of this invention. Such a mechanical device directly couples a patient's eye to the laser's delivery system being affixed to both the laser and the anterior surface of a patient's cornea. The corneal coupling, in these devices, is typically implemented by lowering an applanation fixture over the anterior surface of the cornea under pressure. It is assumed in these forms of devices that pressure applied normal to the corneal surface will restrict conventional motion of the cornea thereby stabilizing the eye along a major access normal to the device.

However, although this assumption may hold true in a large number of cases, it certainly does not have universal application. Moreover, in the cases where it does hold, the device/cornea interface should be established with the iris centered, for best results. The actual establishment of an effective device/corneal interface is an exercise in trial-and-error, resulting in a great deal of frustration to doctor and patient, as well as considerable eye fatigue.

For ophthalmic laser procedures where eye tissue is to be photodisrupted, it is desirable to have proper focus of the laser beam to a specific focal spot in the tissue that is to be affected. Proper focus includes focal definition and proper dimensionality (i.e., the correct spot diameter and shape). To this end, it is helpful for the laser beam to be as free from aberrations as possible. In particular, for ophthalmic laser procedures involving the cornea, the spherical geometry of the cornea can introduce optical aberrations by its shape, and these are separate and distinct from aberrations that may be introduced by the laser optical system. Corneal induced aberrations can distort the definition of the focal spot of a laser beam as the beam is focused to a position within corneal tissue or deeper into the eye, such as the capsular bag or the natural lens.

Due to the spherical geometry of the anterior surface of the cornea, two specific types of aberrations are of particular importance with regard to beam distortion; spherical aberration (which relates to points on the optical axis of the laser beam) and coma (which relates to points that are off-axis). Spherical aberration and coma are similar to one another in that they both arise from a failure to image or focus optical ray traces onto the same point. Spherical aberration relates to a distortion that can be characterized as radial in nature, with some radial directions being stretched while other radial directions are shrunk, converting thereby an ideally circular spot into an elliptical spot. Coma distortion, on the other hand, implies an elongation along one radius a circle, resulting in a "comet-like" shape. Accordingly, any structure which interfaces between a curved, anterior surface of the cornea and laser delivery system will likely encounter such aberration concerns.

In view of the foregoing, it is thus evident that there is a need for a simple mechanical interface device that is able to stabilize the eye against relative motion with respect to a laser beam used for ophthalmic surgical procedures without relying on secondary mechanical considerations, such as surface tension, friction, or the like. Such a device should be able to present an optical feature to an incident laser beam in a stable, well characterized location. In addition to maintaining a proper orientation between the eye and a laser delivery system during ophthalmic laser surgery, such a device should minimize intraocular pressure during the surgical procedure. Such a device should be easy for a clinician to affix, as well as being simple and cost effective to manufacture and use.

SUMMARY OF THE INVENTION

Various apparatus and methods are provided for interfacing an ophthalmic surgical laser with an eye using a patient interface. The interface may include a closed, fluid-filled bladder having fiducials that contacts and deforms to the eye. Alternatively, the interface may have an applanation lens with an outer ring portion and an inner concave portion for receiving the apex of the cornea. A suction ring with a flexible skirt may be used to contact the sclera that is non-circular and/or non-planar. In one version, a lens cone may be co-molded with the attachment ring, with a lens window at the bottom of the lens cone which providing a sealed volume for vacuum-attaching a laser delivery system above the lens cone.

According to the first embodiment, a patient interface for coupling a patient's eye to an ophthalmic surgical laser system comprises a fluid-filled bladder of a flexible material attached to a lower end of a lens cone that is adapted to couple to an ophthalmic laser delivery system. The bladder contains a fixed volume of fluid and has sufficient flexibility to deform upon contact with a patient's eye so as to conform to the cornea. The bladder may define an upper tubular collar and a lower dome-shaped contact portion, wherein the upper collar attaches to a lower ring of the lens cone. The bladder desirably has a wall thickness of between about 25-250 µm, and a refractive index (RI) that is within the range of about 1.35-1.41. To help keep track of patient movement, fiducial markings may be provided on the exterior of the bladder which conform to the cornea when the bladder deforms. For instance, the fiducial markings are lines parallel to the axis of the bladder and lens cone and spaced 90° around the bladder.

In another aspect of the present application, a patient interface for coupling a patient's eye to an ophthalmic surgical laser system comprises an attachment ring configured to overlay an anterior surface of the eye. The attachment ring has a rigid annular housing defining an opening and across which an applanation lens is fixed. The applanation lens has a lower surface defined by an outer ring portion and an inner concave portion shaped to receive the apex of the cornea of the patient's eye when the attachment ring is lowered toward the eye. A boundary between the outer ring portion and the inner concave portion of the lower surface of the applanation lens is preferably a sharp corner. A suction ring may be mounted within the annular housing with downwardly projecting flexible rings for contacting the eye and defining a suction channel therebetween so as to hold the attachment ring to a patient's eye during ophthalmic surgery. The annular housing and suction ring align along a central axis, and an outer one of the flexible rings may define an eye contact surface that is not perpendicular to the central axis. A fluid port may be provided in the annular housing for injection of an index matching fluid above the eye. In one version, a strain relief extension projects radially outward from the annular body on a side of the annular housing on which is located the suction port, and has an aperture for passage of a vacuum tube that connects to the suction port. Furthermore, the applanation lens may be molded together with the rigid annular housing.

The patient interfaces herein may include an attachment ring having a pair of concentric downwardly projecting flexible rings for contacting the eye and defining a channel therebetween, wherein an outer one of the flexible rings defines an eye contact surface that is not perpendicular to the central axis. At the same time, the inner flexible ring defines an eye contact surface that is perpendicular to the central axis. Moreover, the outer flexible ring may define an elliptical eye contact surface, and the inner flexible ring defines a circular eye contact surface.

Another patient interface described herein includes an integral lens cone and attachment ring disposed around a central axis, the attachment ring having a pair of concentric downwardly projecting flexible rings for contacting the eye and defining a channel therebetween and a suction port in communication with the channel. The lens cone includes a lens window fixed across a lower end above the attachment ring. The lens window may be co-molded with the lens cone of a transparent polymer. Fluid injection ports may be distributed around the integral lens cone and attachment ring for injecting an index matching fluid above the flexible rings and below the lens window. Furthermore, an optics ring vacuum may be provided that is sealed to a top end of the lens cone.

A method of preparing a surgical laser system for ophthalmic surgery as described herein includes lowering a fluid-filled bladder of a flexible material attached to a lower end of a lens cone to a patient's eye. The bladder contains a fixed volume of fluid and has sufficient flexibility to deform upon contact with a patient's eye so as to conform to the cornea. The bladder has a closed volume which does not require filling with fluid. The method includes coupling the lens cone to a laser delivery system. The laser delivery system preferably includes an optical tracking system, wherein the method involves registering the tracking system to a plurality of fiducial markings provided on the exterior of the bladder. In one embodiment, the fiducial markings are lines parallel to the axis of the bladder and lens cone and spaced 90° around the bladder.

BRIEF DESCRIPTION OF THE DRAWINGS

Embodiments of this invention will be better understood from the following detailed description when read in conjunction with the accompanying drawings. Such embodiments, which are for illustrative purposes only, depict the novel and non-obvious aspects of the invention. The drawings include the following figures, with like numerals generally indicating like parts:

FIG. 6 is an exploded perspective view of a still further alternative patient interface utilizing a plano-concave applanation lens;

FIG. 7 is an assembled perspective view of the patient interface of FIG. 6;

FIG. 8 is a cutaway perspective view through the patient interface of FIG. 7;

FIG. 9 is a longitudinal sectional view through the patient interface of FIG. 7;

FIG. 10 is a cutaway perspective view of the patient interface of FIG. 7 engaged with an eye of a patient and showing an index matching medium filling a volume therebetween;

FIG. 11 is a schematic view of an eye showing the profile of the nose and intersecting orthogonal planes typically used for geometric orientation to describe parts of the eye, with concentric lines generally indicating the limbal and scleral regions where suction rings contact the eye; while FIG. 11A shows another perspective of the schematic view of the eye shown in FIG. 11;

FIGS. 12A-12D are perspective, elevational, bottom plan and longitudinal sectional views through another patient interface of the present application configured to provide better contact with a non-spherical eye of the patient;

FIG. 13 is a perspective view of a patient interface system for introducing an index matching medium to a patient interface as described in the present application, while FIG. 13A is a longitudinal sectional view of the patient interface system with a vacuum tube removed;

FIG. 14 is a longitudinal sectional view through an exemplary lens cone having a suction ring molded to a bottom end thereof and featuring ports for introducing an index matching medium above the eye.

DETAILED DESCRIPTION OF THE PREFERRED EMBODIMENTS

Embodiments of this invention is directed to a mechanical apparatus that performs the functions of coupling the anterior surface of a target eye to a surgical laser and stabilizing the eye. The apparatus couples the surface of an operative target, such as human corneal tissue, to a mechanical fixture of a surgical laser system, such as the distal tip of a laser beam's delivery system. In the context of a particular embodiment which will be described in greater detail below, the apparatus is affixed both to the anterior surface of a human eye and to the laser delivery system.

Figure 1:
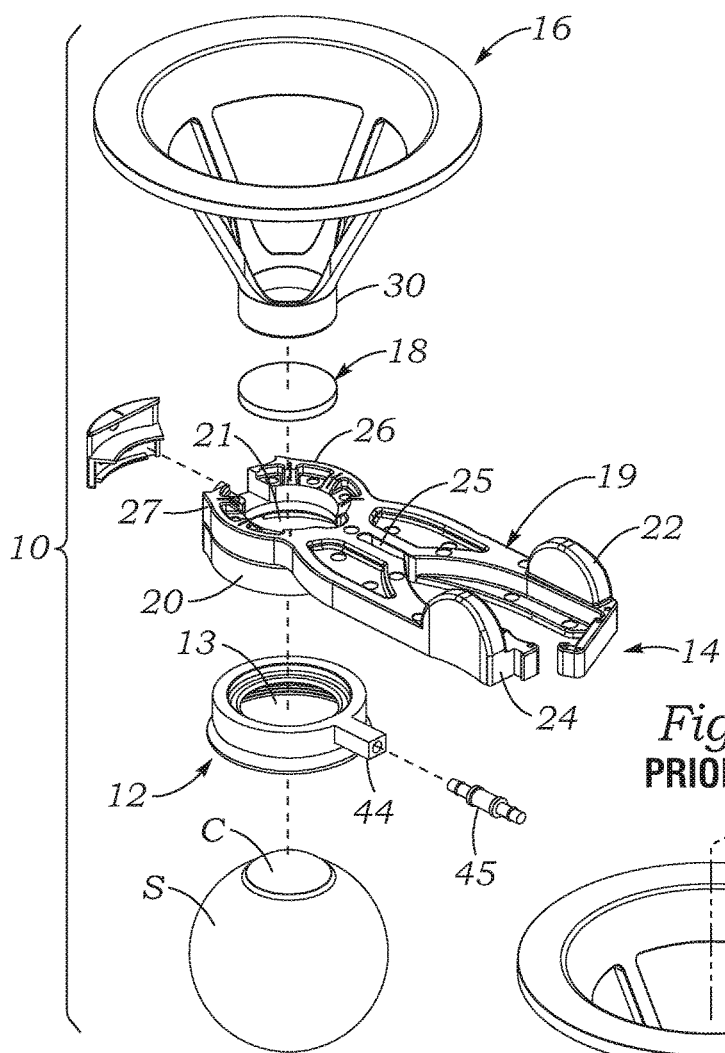
FIG. 1 is a perspective exploded view of a prior art patient interface for use with an ophthalmic laser surgery system.

Referring initially to the exemplary embodiment of FIG. 1, an exemplary ocular stabilization system of the prior art is shown in an exploded, perspective view, and is generally indicated at 10. The description herein of new and improved devices for stabilizing an eye for surgery will be used in the context of the prior art system 10, and thus an overview is appropriate. The eye is shown below the stabilization system 10 having a cornea C and a surrounding sclera S.

The ocular stabilization system 10 (also referred to as a patient interface) is an apparatus that attaches to a human eye and desirably holds (fixes) the eye in all three axes (x, y and z) from translational and rotational movement with respect to the incident beam of a laser surgical device, or at least stabilizes the eye to enable easy tracking thereof. In the prior art, the stabilization system allows for the cornea of the eye to be applanated by a planar lens (laser optic) during a laser surgical procedure, so as to minimize motion of the human eye with respect to the laser optical path.

With reference still to FIG. 1, the prior stabilization system 10 comprises an ocular attachment ring 12 that couples to the eye, a gripper device 14, a lens cone 16 and an applanation lens 18 which, in combination with the lens cone 16, is used to establish an appropriate optical path alignment between the cornea and a laser optical path.

A lower edge of the attachment ring 12 is typically constructed of a flexible, hypoallergenic material such as rubber, hypoallergenic plastic, silicone, or the like. The ring 12 is substantially annular in shape, having a generally smooth exterior surface and a highly articulated and functional inner surface, as will be described in greater detail below. Being annular in shape, the attachment ring 12 necessarily defines an outer diameter (OD) and inner diameter (ID), with the inner diameter circumscribing a central target opening 13.

The gripper device 14 functions much like a clothes pin, and is constructed with an upper gripper portion 19 overlaying a receiver portion 20 designed to receive and contain the attachment ring 12 within the lower portion of a central opening 21 through the gripper device. The gripper portion 19 has two lever handles 22 and 24 separated by a closure spacing 25, and two jaws 26 and 27 surrounding the central opening 21. As the lever handles 22 and 24 are squeezed together, the closure spacing 25 closes and a deformation force is transmitted to the jaws 26 and 27 causing them to widen sufficiently for a cylindrical object to be inserted into the now-widened central opening 21.

The attachment ring 12 is disposed and retained within an appropriately shaped receptacle provided in the underside of the gripper device 14. Since the attachment ring 12 is constructed of a flexible material, the receptacle of the gripper device 14 need only have an ID of a dimension slightly smaller than the OD of the attachment ring, such that the attachment ring may fit within the receptacle and be held in place by compressive force. This allows the attachment ring 12 to be maintained within the central opening 21 of the receiver portion 20, when the jaws 26 and 27 are opened. The jaws 26 and 27 may subsequently be opened to receive a lower apex ring 30 of the lens cone 16 without disturbing or displacing the attachment ring.

Figure 2:
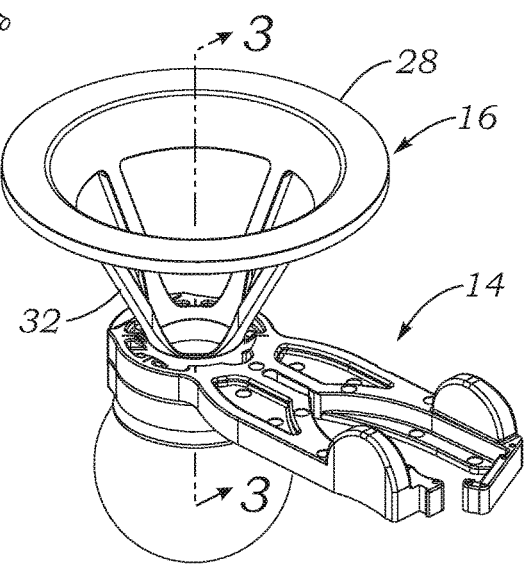
FIG. 2 is a perspective assembled view of the prior art patient interface of FIG. 1 over an eye of a patient.
Figures 3A, 3B:
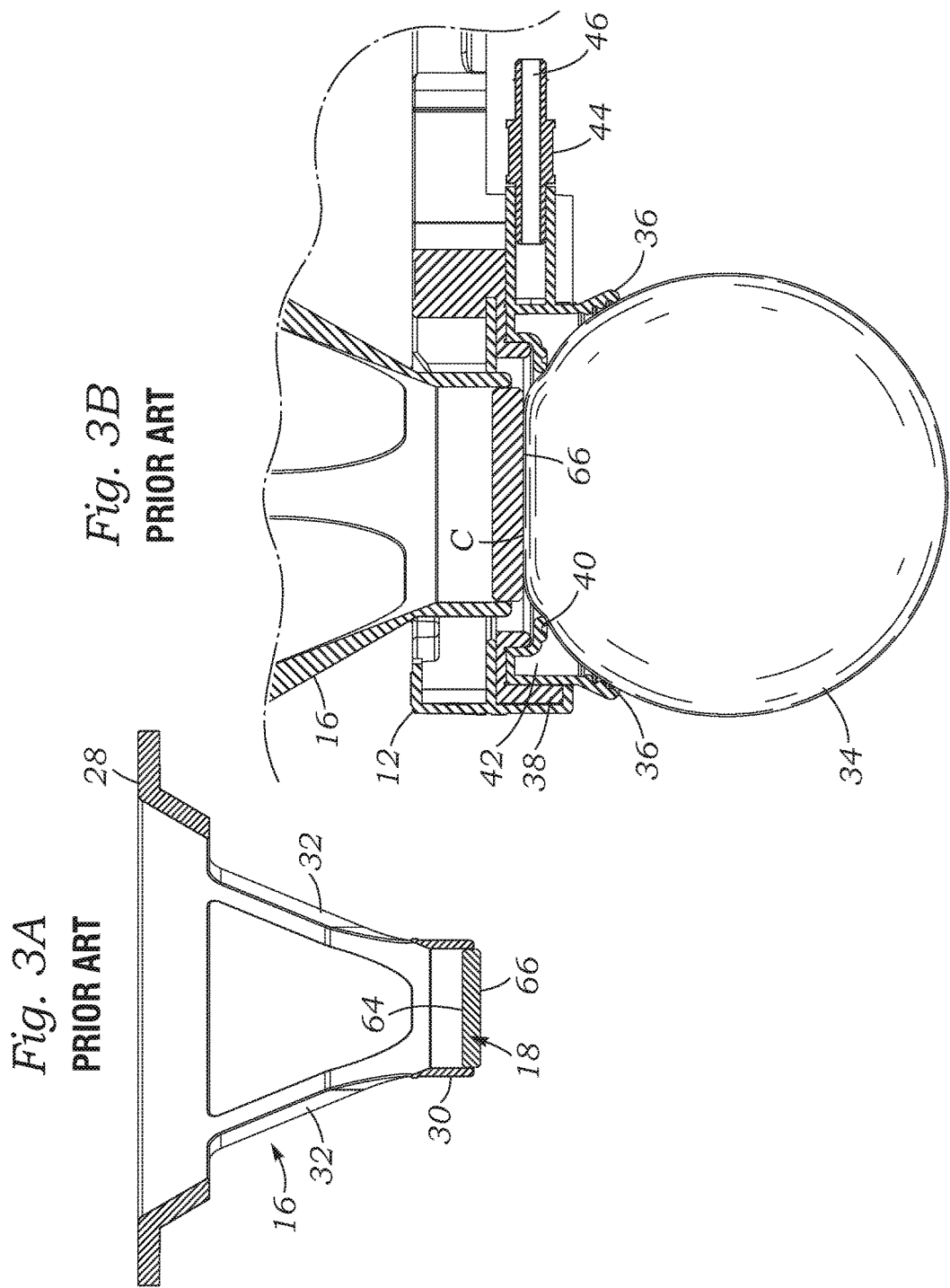
FIG. 3A is a longitudinal sectional view through a lens cone of the prior art patient interface.
FIG. 3B is an enlarged longitudinal sectional view through a portion of the prior art patient interface engaged with an eye of a patient.

In this regard, and in connection with FIGS. 2 and 3A, the lens cone 16 is suitably constructed as an open-sided truncated cone-like structure, with an upper open, annular base ring 28 affixed to the open, cylindrical apex ring 30 by a set of support struts 32 which extend between the base ring 28 and the apex ring 30. The base ring 28 is larger than the apex ring 30 thereby giving the lens cone 16 its characteristic truncated cone-like shape. The base ring portion 28 affixes to the distal end of a laser optical delivery system.

As seen in FIGS. 3A and 3B, the apex ring 30 defines a receptacle for receiving and retaining the applanation lens 18. The apex ring 30 surrounds and retains the applanation lens 18 which is typically bonded into place forming a generally unitary structure with the lens cone 16. The applanation lens 18 is formed with an anterior surface 64 and an applanation surface 66. Both the anterior surface 64 and the applanation surface 66 may be flat and substantially parallel to one another, or concave toward the eye and also parallel to one another. The applanation lens 18 is suitably constructed from a quartz silicate glass or an optical quality plastic chosen for its transmission characteristics of light at the particular wavelength delivered by the laser system under consideration. Although such an applanation lens provides good stabilization, the boundary between the lens and the eye creates an optical discontinuity which affects the accuracy of the laser during surgery, especially for surgeries on the deeper structures within the eye, such as laser cataract surgery.

FIG. 3B show a portion of the ocular stabilization system 10 in cross-sectional form as it would be attached to a human eye 34. The lens cone 16 is coupled to the attachment ring 12, thereby coupling a patient's eye 34 to the laser delivery system, by interfacing the two structures together by the gripper device 14. As the apex ring 30 is inserted into the central opening 21 of the gripper device 14, the applanation surface 66 of the applanation lens 18 makes contact with a presented portion of the anterior surface of the cornea C. As the lens cone 16 is lowered into proximity with the cornea, the applanation surface 66 makes contact with and applies pressure to the cornea C such that when the lens cone is lowered into position, the corneal anterior surface 34*b* and the applanation surface 66 of the lens are in intimate contact with one another over a substantial portion of the applanation surface.

The cylindrical apex ring 30 comprises an inner diameter (ID) and an outer diameter (OD), wherein the OD is dimensioned such that it is only slightly larger than the ID of the central opening 21 of the gripper portion 19 of the gripper device 14. The lens cone 16 is constructed of a substantially rigid material such as a rigid, extruded plastic, aluminum, or the like, such that the OD of the apex ring 30 does not deform under the pressure applied by the jaws 26 and 27 of the gripper portion 19. Accordingly, the apex ring 30 does not initially fit into the ID of the central opening 21 of the gripper device 14. Compressive force applied to the lever handles 22 and 24 causes the jaws 26 and 27 to open and the interior diameter of central opening 21 to increase such that OD of the apex ring 30 may be inserted into the central opening 21 of the gripper device 14. When pressure is released on the lever handles 22 and 24, the jaws 26 and 27 close upon the apex ring 30 thereby establishing a fixed relationship between the lens cone 16 and the gripper device 14. Since the gripper device 14 is in geometric engagement with the attachment ring 12, and since the attachment ring 12 is coupled to corneal tissue, it should be understood that the lens cone 16 is now held in a particular spatial relationship (alignment) with the surface of the cornea.

With reference still to FIG. 3B, the attachment ring 12 provides a primary interface with the corneal portion C of a human eye 34 and a laser delivery system. The attachment ring 12 includes a soft annular member 35 having a lower skirt 36 which functions as a shroud that comes into intimate contact with the anterior portion of the human eye 34. The shroud 36 has a relatively thin cross-section and is deformable (e.g., silicone) so as to establish and maintain conformal contact with the anterior corneal surface C. The annular member 35 extends upwardly from the skirt portion 36 and fits closely with any downward-opening channel formed partly by an outer wall 38 in the receiver portion 20. The close fit of the annular member 35 in the channel maintains a substantially uniform ID against deformations of the lower shroud portion 36 in response to pressure against the shroud portion by the human eye 34.

The attachment ring 12 further includes an interior, annular ring member 40 which protrudes inwardly toward the target opening 13 (FIG. 1). The annular ring member 40 has a bottom surface that defines a downwardly-opening cavity 42 within the periphery of the skirt portion 36. The attachment ring 12 further includes an attachment fitting 44 extending radially outward. The attachment fitting 44 includes a central orifice 46, disposed along its entire length, and which passes through the material of the attachment ring's skirt portion 36 (not shown) such that a communication path is opened between the annular channel 42, at one end, and the distal end of the attachment fitting 44. As seen in FIG. 1, the attachment fitting 44 might be accessed by inserting one side of a male-to-male fitting coupler 45 into the central orifice 46 and coupling the other side to a length of small diameter, medical grade tubing. The tubing is then coupled to a vacuum source which, in turn, is then able to apply a vacuum to the annular channel 42.

With reference still to FIG. 3B, the applanation surface 66 provides a reference surface from which the laser system is able to compute a depth of focus characteristic. In embodiments where the applanation surface 66 contacts the corneal surface, as shown, the position of the applanated corneal surface C with respect to the laser delivery tip is known from the known position of the applanation surface. It is, therefore, a relatively straightforward matter to focus a laser beam to any point within the cornea.

In other embodiments, tomography techniques (e.g., optical coherence tomography) or other ranging technology can be used to determine the relative location and position of various ocular structures, including the anterior corneal surface, the various corneal layers (e.g., epithelium, endothelium, Descemet's membrane, stroma, and Bowman's layer), the capsular bag, the lens, the retina, and the like. Using tomography or other ranging techniques, the relative location and position of the laser delivery tip with respect to such structures can be determined and thus, the depth of the laser beam can be determined and calibrated into acceptable tolerances equivalent to the aforementioned tolerances for alignment or tolerances associated with conventional microkeratomes. In such embodiments, the tolerances associated with the dimensions of the lens cone, alignment of the applanation lens, and the like, may have greater acceptable ranges.

In operation, the attachment ring 12 is placed around the limbus of a patient's eye 34, such that its lower, skirt portion 36 surrounds the anterior surface of the cornea 34*a*, thereby leaving free optical access to the cornea 34*a*. In other embodiments, the attachment ring 12 has an ID of a dimension that permits placement of the attachment ring 12 around a portion of the sclera of a patient's eye 34. A slight compressive force is applied to the attachment ring 12, thereby deforming the skirt portion 36 in an outwardly direction, such that it tends to conform to the shape of the corneal surface. A slight vacuum is developed by a vacuum source or suction pump and coupled to the attachment ring 12 through the attachment fitting 44. As suction is applied to the attachment fitting 44, its internal orifice 46 couples the suction to the annular channel 42 which is now sealed-off from the external ambient environment by corneal, limbal, or scleral contact.

With the eye so presented and held in place by the attachment ring 12, the lens cone 16 and applanation lens 18 can be lowered into proximity or actual contact with the cornea, and retain the lens cone, and particularly the applanation lens, in position by fixing the apex ring 30 with the gripper device 14. The gripper device 14 is opened to receive the lens cone 16 which is then lowered into the attachment ring 12. The gripper device 14 is then closed, thereby clamping the lens cone 16 in position and fixing the applanation lens 18 relative to the cornea.

As should be understood from the foregoing, and with respect to the exemplary embodiments, the stabilization system is substantially rigidly coupled to the laser delivery system, thus the plane of the applanation surface 66 is characterizable in space with respect to any given focal point of an incident laser beam. With regard to the eye, it should be understood that the lens 18 is able to be positioned in the "z" direction due to the flexibility of the skirt portion 36 of the attachment ring when the ring is opened. The applanation lens 18 is therefore able to accommodate variously shaped corneal surfaces without placing undue pressure on the eye and achieve a variable degree of flattening of the cornea. The applanation lens 18 is thusly secured against motion and is accurately disposed in a stable "x-y-z" plane with respect to the eye.

Ophthalmic Surgery Patient Interface with Fluid-Filled Applanation Bladder

In addition to the optical discontinuity created by contact between the applanation surface 66 and the cornea, other problems with direct contact applanation lenses include increased intraocular pressure from the suction ring and downward pressure on the eye by the applanation lens 18, corneal wrinkles from flat or curved applanation lenses when the corneal curvature is not well matched with the applanating cone, and the need to physically dock with the eye. Consequently, the present application provides several solutions which address one or more of these drawbacks.

Figure 4:
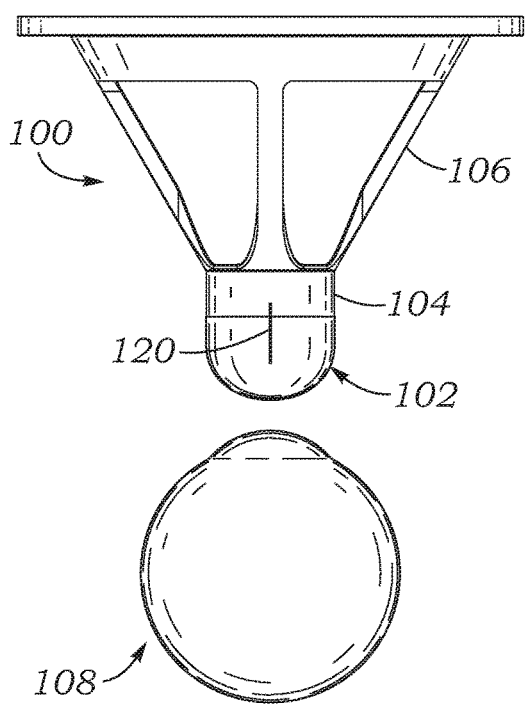
FIG. 4 is an elevational view of an alternative patient interface having a fluid-filled bladder above an eye of the patient.
Figure 5:
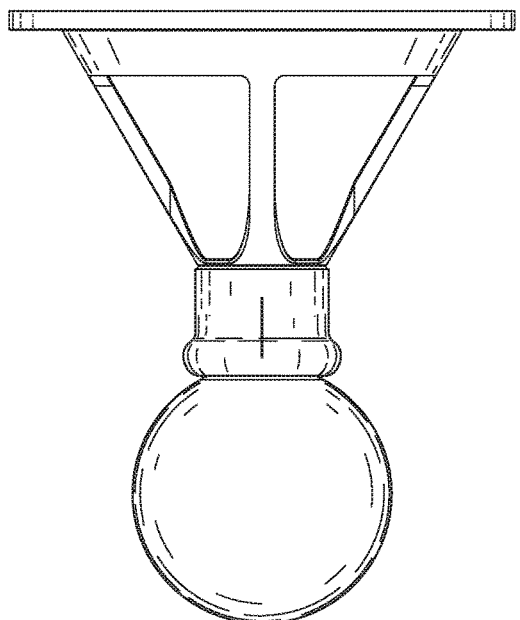
FIG. 5 is an elevational view of the patient interface of FIG. 4 shows a fluid-filled bladder in contact with an eye of a patient.
Figure 4A:
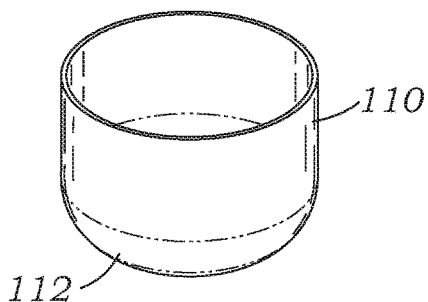
FIG. 4A is a perspective view of the bladder in isolation.
Figure 5A:
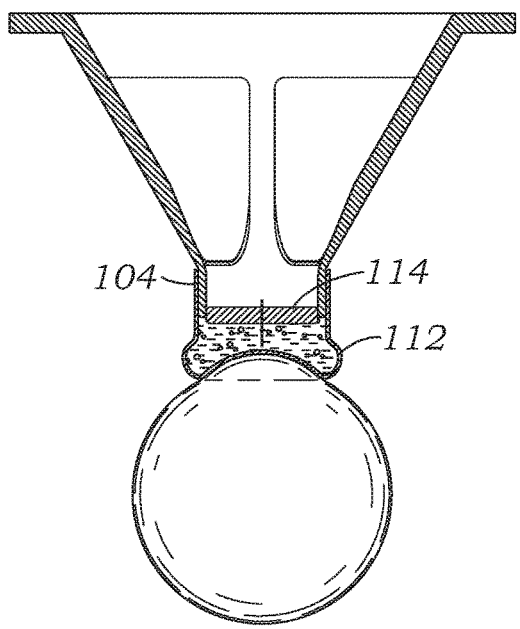
FIG. 5A is a longitudinal sectional view of the patient interface showing the deformed bladder in contact with the eye.

In a first embodiment, a patient interface 100 seen in FIGS. 4-5 utilizes a compliant liquid-filled bladder 102 attached to the lower apex ring 104 of a lens cone 106. The bladder 102 directly contacts the eye 108, as seen in FIG. 5, and provides some stability thereto during ophthalmic laser surgery. As seen in FIG. 4A, the bladder 102 is desirably made from a thin, compliant plastic or silicone material having an upper tubular collar 110 and a lower dome-shaped contact portion 112. The collar 110 is held on the exterior of the apex ring 104, such as by adhesives or mechanical clamping (not shown) creating a sealed volume above the bladder and below a lens cone glass surface 114.

The volume within the bladder 102 is partially filled with a transparent fluid having an optical refractive index (RI) that is close to or equal to the RI of the cornea. This RI matching reduces optical distortion experienced by the laser beam when passing through the bladder/cornea interface. In one embodiment, the bladder 102 is filled with 0.5 mL transparent solution at atmospheric pressure. The transparent solution can be water, a balanced salt solution, an ophthalmic viscoelastic, or other optically suitable solution. The refractive index RI (or index of refraction) of a medium is a dimensionless number that describes how light propagates through it. RI is defined as $$RI = c/v,$$

where c is the speed of light in vacuum and v is the speed of light in the medium. For example, the RI of water is 1.33, meaning that light travels 1.33 times as fast in vacuum as it does in water. In most studies, the aqueous and vitreous humors both have a refractive index of 1.336-1.339, whereas the cornea has an RI of 1.376-1.41. Glass, used typically for the applanation lenses described above, has an RI of between about 1.5-1.6. Flexible materials such as silicone that may be used for the bladder 102 typically have RIs of greater than 1.4.

An example of a material potentially usable as a suitable bladder material is a fluoropolymer called THV (Tetrafluoroethylene hexafluoropropylene vinylidene fluoride), whose refractive index is 1.35. Other materials such as silicone rubber whose refractive index is approximately 1.40 may be used. Alternatively, a medical grade, flexible, elastic, clear polyurethane may be used. The material preferably has a refractive index that is as close as possible to the RI of the cornea, and thus is preferably between about 1.35-1.41. The RI of the transparent solution within the bladder is between about 1.33-1.41. For instance, the RI of three readily available contact lens solutions, AMO LENS PLUS™ OcuPure™, BAUSCH & LOMB Sensitive Eyes™ Plus Saline Solution, and Sauflon saline, are 1.3347, 1.3348 and 1.3348, respectively.

The wall thickness of the dome-shaped portion 112 of the bladder 102 is desirably extremely small to further minimize any optical distortion from the laser beam passing through. In one embodiment, the wall thickness of the dome-shaped portion 112 is between about 25-250 µm, more preferably between about 25-100 µm or even more particularly 38-75 µm. In terms of candidate materials, if a fluoropolymer such as THV is used the wall thickness of the dome-shaped portion 112 is desirably between about 25-75 µm, and if a polyurethane is used the thickness will desirably be either 1 mil (25 microns) or 1.5 mil (38 microns).

The patient interface 100 having the fluid-filled bladder 102 does not require a surrounding suction ring, as described above, so the working diameter defined by the surface area of the bladder in contact with the eye may be increased outward past the cornea to the limbus, or further. In use, the surgeon lowers the patient interface 100 onto the eye until the bladder 102 deforms. Further advancement conforms the bladder 102 to the contours of the cornea and lids. Any pressures generated against the eye are distributed across all surfaces (cornea and lids), thus reducing intraocular pressure increases and corneal wrinkles as compared to an applanation lens as described above.

In a preferred embodiment, fiducial markings 120 are provided on the exterior surface of the bladder 102 to serve as targets for eye tracking systems, such as a CCD based video system. For example, four evenly spaced vertical markings 120 may be provided on the exterior of the bladder 102 within both the tubular collar 110 and dome-shaped contact portion 112. The fiducial markings 120 are sufficiently low down on the bladder 102 so as to conform to the cornea when the bladder deforms, thus presenting more horizontal "cross-hairs" for a tracking system. This provides quadrant markings for the tracking system. If the eye moves during surgery, the quadrant markings 120 also move, which allows the tracking system to accommodate the movement and readjust the aim of the laser. The markings 120 may be etched into the exterior surface of the bladder 102, or maybe printed thereon. The fiducial markings 120 are more distinct and predictable than the eye's natural features, thus requiring less complex image processing algorithms and translating into lower equipment and bill of materials cost.

In a preferred embodiment, the bladder 102 is attached to the patient interface lens cone 106 as shown. Alternatively, the bladder 102 is constructed as a separate part, independent of the patient interface lens cone 106, sandwiched between the eye and the apex ring 104 of the lens cone. In the latter configuration, the bladder 102 will be placed on the cornea just prior to lowering the lens cone 106 for applanation.

Ophthalmic Surgery Patient Interface with Plano-Concave Applanation Lens

FIGS. 6-10 illustrate a second embodiment of a patient interface for ophthalmic laser surgery including a modified receiver portion 150 and attachment ring 152. The receiver portion 150 is relatively rigid, while the attachment ring 152 is soft and flexible. The attachment ring 152 is similar to the attachment ring 12 described above for the prior art system 10 and provides a vacuum seal against the eye.

As seen in the exploded view of FIG. 6 and also with reference to the sectional view in FIG. 8, the receiver portion 150 includes an upper housing 160 having a downwardly opening channel 162 that receives therein an annular portion 164 of the attachment ring 152. The ring 152 includes an outer skirt 166 and an inner ring member 168, with an annular vacuum manifold 170 therebetween. The manifold 170 opens to passages that lead to a vacuum port 172. As seen in FIG. 10, lowering the attachment ring 152 to the surface of the eye causes the skirt 166 and ring member 162 form a seal around the annular manifold 170, such that a vacuum pulled through the port 172 affixes the structure to the eye.

The receiver portion 150 and attachment ring 152 provide an interface between the eye and a laser delivery system, which may be mounted to an upper end of a lens cone as described above. The patient interface further includes a modified applanation lens 178 that contacts the eye and through which the laser passes.

The applanation lens 178 shown in diametric section in FIG. 8 includes a planar upper surface 180, and a lower surface having a planar outer ring 182 and a concave inner recess 184. The inner recess 184 receives the apex of the cornea and the applanation lens 178 is in contact with the eye. Although the transition between the outer ring 182 and inner recess 184 is shown distinctly as an abrupt corner, it may be rounded to reduce any optical artifacts. The presence of the inner recess 184 aids in fixing the corneal surface during laser surgery without unduly increasingly intraocular pressure in the eyeball. The combination of both flat and concave surfaces tried to better fit the range of patients while still providing enough depth registration to ensure proper laser treatments.

The applanation lens 178 may be a separate element held or adhered into the rigid housing 160 of the receiver portion 150, or it may be molded with the housing 160 as shown. In the former case, the materials may vary from glass to polymer, preferably an acrylic similar to contact lens materials. If the applanation lens 178 is molded into the housing 160 as single piece, as shown, the material is preferably acrylic with as close a refractive index (RI) to the corneal RI as possible.

FIG. 9 shows the inner recess 184 as a partial sphere, although other curvatures such as partial ellipsoids or variable axis curves are contemplated.

Any mismatch between the surfaces of the applanation lens 178 and the patient's cornea or sclera will be filled with an index matching liquid to ensure the optical path is as consistent as possible to produce proper focal volumes of laser radiation.

FIG. 10 illustrates the applanation lens 178 in contact with a corneal surface C of an eye, with an index matching liquid 190 provided in the volume underneath the lens not in contact with the eye. As before, the attachment ring 152 provides the soft sealing skirt and vacuum manifold therein for securing the ring to the eye. The index matching liquid 190 fills the space above the sealing skirt had outside of the inner recess 184. In one embodiment, a liquid filling port 192 is provided in the attachment ring housing 160 leading to internal channels and eventually the volume under the applanation lens 178 and surrounding the eye.

Trading the larger flat or concave applanation lens of the prior art with the applanation lens 178 having a planar-concave lower surface provides only partial contact and compression of the eye, which results in a number of benefits. Since intimate contact between the applanation lens 178 over the entire corneal surface does not occur, a method to determine the location of the corneal surface or deeper surfaces will be needed in order to reliably focus the laser energy to the proper location. For example, optical coherence tomography or some other range finding system will be utilized. Furthermore, by registering only a portion of the corneal surface against the lower surface of the applanation lens 178, heart beat pulsations transmitted through the eye will be lessened for more stability and thus better surgical outcomes.

Depending on the diameter of the inner recess 182 and its curvature, the volume of the eye that is compressed and varies. In general, as the diameter of the inner recess 182 increases the volume increases. Likewise, as the radius of concave curvature of the recess 182 increases the recess becomes flatter and generally the volume compressed increases. The partial applanation provided by the lens 178 provides positional stability so the surgeon can do intrastromal arcuate incisions with no need of real-time tracking of the cornea position.

It should be noted that although the outer ring 182 of the lower surface of the applanation lens 178 is shown and described as planar, other configurations are possible. For example, the outer ring 182 may be concave or even convex, depending on the requirements of the optical system.

Ophthalmic Surgery Patient Interface with Non-Circular Suction Ring

Often when fixing laser surgery devices to the eye, the intraocular pressure builds up from pressing down on the eye with the suction ring. Such suction rings are uniformly circular, although the limbal or scleral surfaces of the eye are not quite spherical. This mismatch often results in multiple attempts at docking the vacuum ring, and deformation of the eyeball in order to fit the circular ring to it. Distortion of the eyeball adds to intraocular pressure, and also increases the likelihood of failure of the suction ring during use of the device. Furthermore, certain eyes such as those having astigmatism, are less than spherical in shape and thus present difficulties for circular sealing rings.

FIG. 11 is a schematic view of an eye showing the profile of the nose and orthogonal planes intersecting along the optical axis through the eye. Outer portions of the four planes indicate the conventional meridian directions used for geometric orientation to describe parts of the eye. In the horizontal plane, the nasal direction (N) is toward the nose (seen in profile) while the temporal (T) direction is to the outside. As usual, superior (S) is up and inferior (I) is down. FIG. 11A indicates the same meridian directions looking straight along the optical axis and also showing the intermediate azimuth planes (NS, NI, TI, TS) rotated 45° from the primary planes.

With reference again to FIG. 11, a first topographical line 200 is drawn on the eye and generally indicates the center of the limbal region. The line 200 represents the intersection of the surface of the eyeball with an infinite number of planes around the azimuth through the optical axis similar to the orthogonal planes show. The line 200 is drawn at a certain diameter outward from the optical axis. A second topographical line 202 drawn on the eye generally indicates the beginning of the scleral region, or at least a contact location within the scleral region for the outer skirt of a suction ring of a patient interface. The location of the limbal and scleral regions radially outward from the optical axis are determined from an average population. Again, the line 202 represents the intersection of the surface of the eyeball with an infinite number of planes through the optical axis similar to the orthogonal planes shown, and again at a certain diameter outward from the optical axis. Measurements of the tangent angles (to the eye surface) at the lines 200, 202 reveal that the eyeball in the limbal and scleral regions is not a perfect sphere. In general, the first topographical line 200 in the limbal region is more planar than the second topographical line 202 in the scleral region, and the tangent angles on the nasal side have a measurably lesser slope as compared to the temporal side. That is, with reference to FIG. 11A, the tangent angles measured at N, NS, and NI in the scleral region were statistically less than those measured on the temporal side, which were essentially equal around I-TI-T-TS-S. Additionally, the tangent angles measured in the limbal region were statistically equal around the entire eye.

Consequently, one solution to the mismatch between current circular suction rings and non-spherical eyeballs is illustrated in FIGS. 12A-12D which shows a patient interface 210 in which at least a portion of the suction ring is non-circular and/or non-planar. The patient interface 210 includes a generally annular body 212 which may have internal features such as tabs 214 (or threads) for connecting to a lens cone, such as those described earlier. On the lower end of the housing, the patient interface 210 has an outer skirt 220 separated from an inner ring 222 by a suction channel 224. As seen in the sectional view of FIG. 12D, a suction port 226 is shown that leads to internal passages in communication with the suction channel 224. The patient interface 210 functions in a similar manner as those described above, with the outer skirt 220 and inner ring 222 sealing against the surface of the eyeball such that a negative pressure can be formed therebetween by applying a vacuum to the suction port 226. A flexible tube (not shown) attached to the suction port 226 desirably passes through an aperture 230 of a strain relief extension 232 projecting radially outward from the annular body 212.

FIG. 12B shows the patient interface 210 from the side. Because of the outwardly projecting strain relief extension 232 and attached vacuum tube (not shown), the right side in FIG. 12B would be positioned to the temporal side of the patient, with the left side corresponding to the nasal side. This configuration can be used on either eye by simply reorienting by 180° the patient interface 210.

The angle θ indicates material removed from the lower edge of the outer skirt 220 of the sealing apparatus. In one embodiment, the angle θ is less than 2°, more preferably less than 1°, and in one exemplary embodiment is 0.73°. The material removed may result in a planar surface defined by the lower edge of the outer skirt 220, or a non-planar surface. In an exemplary embodiment, the lower edge of the outer skirt 220 defines a plane at the angle θ. Looking from the bottom of the patient interface 210 at the slight angle θ, as in FIG. 12C, the periphery of the outer skirt 220 defines an ellipse with a major axis generally aligned in the nasal-temporal (N-T) direction, and the minor axis perpendicular thereto, or in the superior-inferior (S-I) plane. This is because the annular body 212 and outer skirt 220 are annular, and cutting across a tube with an angled plane creates an ellipse. This non-circular shape better fits the actual shape of the eyeball, and thus helps ensure quicker and more secure engagement of the patient interface 210 therewith.

Figure 12C:
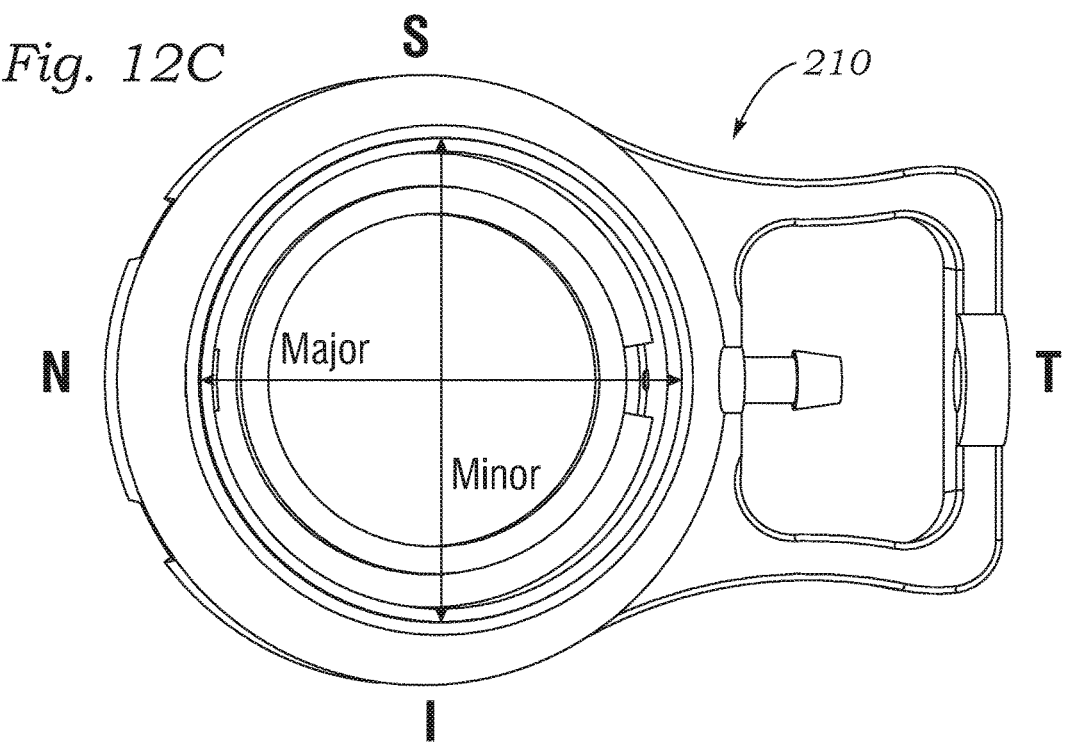
Figure 12D:
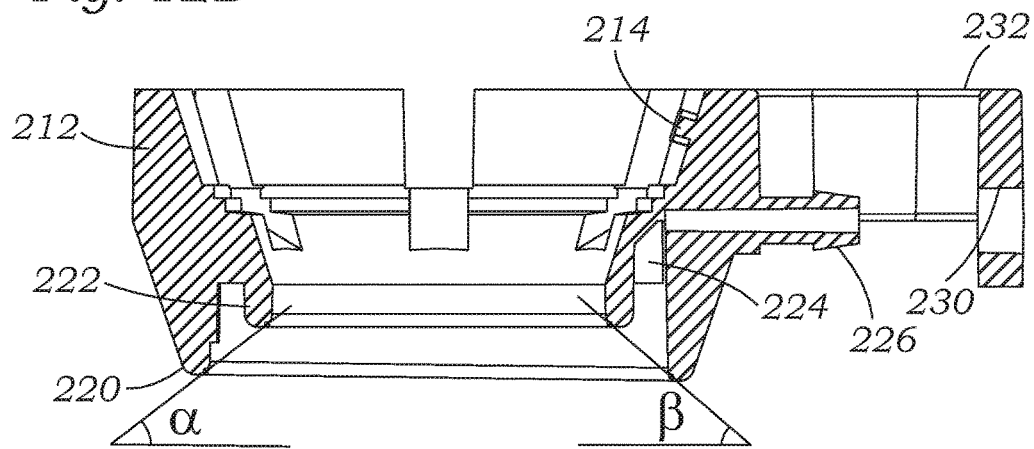

FIG. 12D illustrates several angles drawn tangent to the curve lower edges of the outer skirt 220 and inner ring 222. More particularly, an angle α and an angle β both lie in the nasal-temporal plane, with the former on the nasal (N) side and the latter on the temporal (T) side. Because material has been removed from the nasal (left) side of the skirt 220, α<β. More such angles tangent to both the outer skirt 220 and inner ring 222 can be drawn around the azimuth which will be in between these two extremes. For example, angles adjacent to the angle α on the nasal side and continuing toward the temporal side will gradually increase until they equal the angle β. Or, as mentioned above, the change in the angles drawn between the outer skirt 220 and inner ring 222 may change non-linearly.

Since the outer skirt 220 typically contacts the eyeball in the scleral region, material is removed to make it non-planar and ellipsoid so as to better fit the measured topography of the scleral region. On the other hand, the inner ring 222 contacts the eyeball in the limbal region, which having a relatively planar and circular topography, and so the inner ring 222 remains planar, horizontal and thus circular on its lower edge. Thus the patient interface 210 annular suction region is bounded by the inner ring 222 which is essentially circular and the outer ring 220 which is slightly elliptical.

Looked at another way, the lower edges of the outer skirt 220 and inner ring 222 are desirably shaped to conform to the actual shape of an eyeball based on empirical measurements. This means that the scleral region on the nasal side has a shallower angle, and for a given radial distance outward from the optical axis it will be axially closer to the apex of the cornea than will a point in the scleral region on the temporal side. Therefore the material on the nasal side of the skirt 220 is removed. As the patient interface 210 is lowered onto the eyeball with its own axis coincident with the optical axis, both the nasal and temporal sides of the outer skirt 220 will contact the eyeball the same time, in the ideal situation. Of course, the empirical measurements represent an average across a population, and there may be some variance between patients, but the overall outcome is a better fit to the average eye.

FIG. 13 is a perspective view of an integrated patient interface system 250 above an eye 252, while FIG. 13A is a longitudinal sectional view with a vacuum tube 254 removed. The system 250 combines the aspects of the sealing ring with the lens cone, the latter also being integrated with the delivery optics. In an overview, a lens cone 260 couples to the bottom end of an optics ring 262, and incorporates a sealing ring 264 on its lower end. The sealing ring includes a vacuum port 266, such as those described above, for connection of the vacuum tube 254. As seen best in the sectional view of FIG. 13A, the combined lens cone 260 and sealing ring 264 provide one or more fluid inlets 270 through which an index matching medium can be introduced, such as with a handheld bottle 272.

As seen best in FIG. 14, the lower end of the sealing ring 264 includes a pair of flexible skirts or rings 274 between which is an annular channel (not numbered) in communication with the vacuum port 266. The sealing ring 264 functions similar to those described above, and thus secures the patient interface system 250 to the eye 252 when suction is pulled through the vacuum tube 254 and port 266. In a preferred embodiment, a housing of the sealing ring 264 is co-molded of a rigid polymer with the lens cone 260, and the lower skirts 274 are formed by a soft separate piece that is fitted to a recess in the housing. Alternatively, a solid sealing surface may be substituted.

The optics ring 262 includes a lower seal 280 that mates with an outward flange ring 282 of the lens cone 260. The lower end of the lens cone 260 is closed by a lens window 284. Although not shown, an upper end of the optics ring 262 will be sealed such that suction pulled through a vacuum port 286 secures the optics ring to the top of the lens cone 260. This provides a large coupling force for relatively small vacuum pressure due to the large effective seal area. Although shown schematically, optics 288 protrude downward into the lens cone 260. With reference again to FIGS. 13A and 14, the fluid inlet(s) 270 molded into the lens cone 260 assembly allow liquid entry below the lens window 284 and above the eye 252.

There are two possible configurations for the lens cones described herein; either there is a "permanent cone" that is part of the laser delivery system, or the cone is part of the disposable patient interface.

In a preferred embodiment, the assembly of the lens cone 260 and sealing ring 264 is made of a disposable rigid plastic. Desirably, the material is optically clear so that the lens window 284 can be molded at the same time. In the earlier embodiments, the lens cone was made separate from the sealing ring, with the sealing ring containing an applanation lens or other such lens window. Therefore, the separate sealing ring was the part that contacts the patient, and thus was disposable. However, the patient interface system 250 reduces the number of steps required to assemble for surgery, For a "permanent cone," the disposable patient interface would just have to attach to it, either with a twist-lock, a thread, suction, magnets, clamps, or some other mechanical means, such as shown below in FIGS. 15A and 15B. The disposable patient interface would have to have the lens window as a part of it, to maintain sterility and disposability. Further, there would need to be a way to get liquid into the space directly above the eye and below the window, either via a port or a channel.

Alternately the cone is integrated with the disposable patient interface, and the conical part exists only to allow attachment someplace above the lowest optical element. This is the embodiment shown above in FIGS. 13-14. The cone shape is not necessary, and the shape could be cylindrical or otherwise to allow attachment to the laser delivery system, either at predetermined locations (clocked) or in an orientation selectable by the user. The cone would be attached to the laser system either with a twist-lock, a thread, suction, magnets, clamps, or some other mechanical means. Again, there would have to be a system for injecting liquid in the region under the window and above the eye.

In all these designs the patient interface grips securely onto the eye with some suction element in order to secure the eye and prohibit it from movement. Alternatively, a coffer dam could be used which makes contact with the eye and contains the liquid. If means to track the eye movement is includes then suction might not be necessary, but tracking systems add complexity and cost to the system.

Figure 15A:
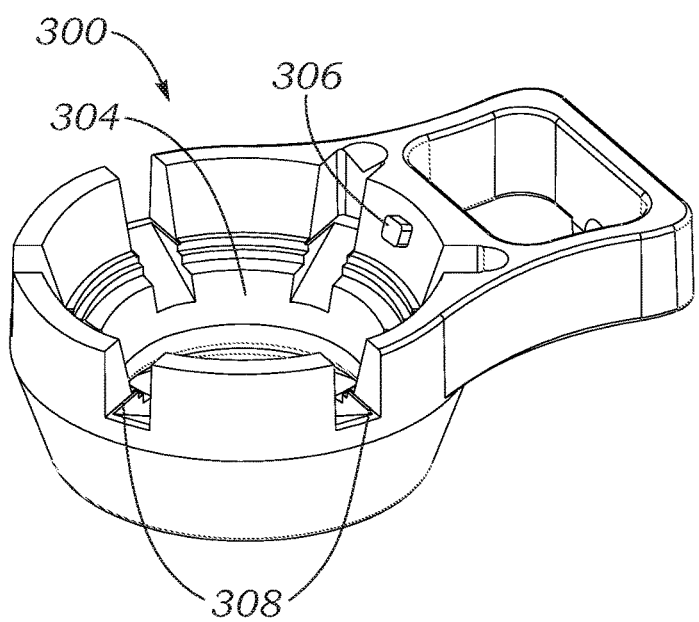
FIGS. 15A and 15B are perspective views of two different attachment rings for coupling with the lens cones described herein.
Figure 15B:
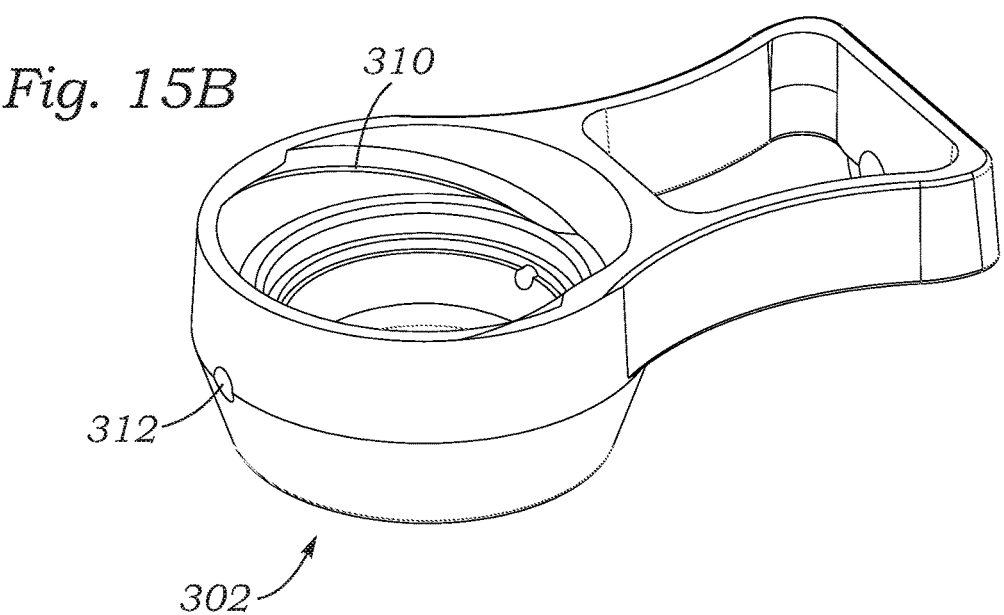

FIGS. 15A and 15B are perspective views of two different disposable attachment rings 300, 302 coupling with the lens cones described herein. The first attachment ring shows a recess 304 for receiving the lower end of the lens cone, and has an inwardly projecting tab 306 mirrored by a second opposite tab (not shown). The tabs 306 are used to engage bayonet-type channels or other such locking structure. Furthermore, the ring 300 features a plurality of generally axially-oriented notches 308 which provide passages for manually injecting an index matching medium above the sealing rings and eye, but below a lens window. The lens window (not shown) is desirably held in an upper part of the attachment ring recess 304 and is thus disposable therewith.

The attachment ring 302 in FIG. 15B includes a 2-start thread 310 to enable it be screwed onto a permanent feature on a lens cone. An inlet port 312 permits liquid to be injected through a port parallel to the vacuum port.

It should be understood that individual components of the various patient interfaces described herein may be combined with other systems than those in context of which they were described. For instance, the angled or non-circular suction rings could be combined with the plano-concave applanation lens or by integrated into the system having the suction ring and lens cone co-molded. Likewise, the fluid-filled bladder and lens cone could include structure at the upper end of the lens cone for coupling to a laser delivery system using a vacuum. The permutations are numerous and only excluded by physical barriers to such combination.

Although embodiments of this invention are described and pictured in an exemplary form with a certain degree of particularity, describing the best mode contemplated of carrying out the invention, and of the manner and process of making and using it, those skilled in the art will understand that various modifications, alternative constructions, changes, and variations can be made in the ophthalmic interface and method without departing from the spirit or scope of the invention. Thus, it is intended that this invention cover all modifications, alternative constructions, changes, variations, as well as the combinations and arrangements of parts, structures, and steps that come within the spirit and scope of the invention as generally expressed by the following claims and their equivalents.

What is claimed is:

1. A patient interface for coupling a patient's eye to a surgical laser system, the patient interface comprising: an attachment ring, disposed around a central axis, configured to overlay an anterior surface of the eye, the attachment ring having a pair of concentric downwardly projecting flexible rings for contacting the eye and defining a channel therebetween and a suction port in communication with the channel, the pair of flexible rings including an outer skirt and an inner ring, wherein a lower edge of the outer skirt defines a planar surface that is not perpendicular to the central axis.

2. The patient interface of claim 1, wherein a lower edge of the inner ring defines a plane that is perpendicular to the central axis.

3. The patient interface of claim 2, wherein the lower edge of the inner ring defines a circular outline in the plane that is perpendicular to the central axis.

4. The patient interface of claim 1, wherein the lower edge of the outer skirt defines an elliptical outline in the planar surface that is not perpendicular to the central axis.

5. The patient interface of claim 4, wherein the elliptical outline defined by the lower edge of the outer skirt has a major axis parallel to a direction from the central axis to the suction port and a minor axis perpendicular to the direction from the central axis to the suction port.

6. The patient interface of claim 1, wherein the attachment ring is co-molded with a lens cone having a lens window fixed across a lower end above the attachment ring.

7. The patient interface of claim 1, wherein an angle between the planar surface defined by the lower edge of the outer skirt and a plane perpendicular to the central axis is less than 2 degrees.

8. The patient interface of claim 7, wherein an angle between the planar surface defined by the lower edge of the outer skirt and the plane perpendicular to the central axis is 0.73 degrees.

9. The patient interface of claim 1, wherein in a cross-section that passes through the central axis and the suction port, the planar surface defined by the lower edge of the outer skirt is tilted downwards on a side of the suction port.

10. The patient interface of claim 1, wherein a first angle defined between a plane perpendicular to the central axis and a straight line connecting the lower edge of the outer skirt and a lower edge of the inner ring at respective first circumferential locations opposite the suction port is different from a second angle defined between the plane perpendicular to the central axis and a straight line connecting the lower edge of the outer skirt and the lower edge of the inner ring at respective second circumferential locations aligned with the suction port.

11. The patient interface of claim 10, wherein the first angle is less than the second angle.

12. A patient interface for coupling a patient's eye to a surgical laser system, the patient interface comprising:

an attachment ring disposed around a central axis configured to overlay an anterior surface of the eye, the attachment ring having a pair of concentric downwardly projecting flexible rings for contacting the eye and defining a channel therebetween and a suction port in communication with the channel, the pair of flexible rings including an outer skirt and an inner ring, wherein a first angle defined between a plane perpendicular to the central axis and a straight line connecting a lower edge of the outer skirt and a lower edge of the inner ring at respective first circumferential locations opposite the suction port is different from a second angle defined between the plane perpendicular to the central axis and a straight line connecting the lower edge of the outer skirt and the lower edge of the inner ring at respective second circumferential locations aligned with the suction port.

13. The patient interface of claim 12, wherein the first angle is less than the second angle.

* * * * *